United States Patent [19]

Dear et al.

[11] 4,158,672

[45] Jun. 19, 1979

[54] POLYFLUOROALKYLTHIO ALCOHOLS, ESTERS AND USEFUL COMPOSITIONS THEREFROM

[75] Inventors: Robert E. A. Dear, Mt. Kisco, N.Y.; Neal O. Brace, Wheaton, Ill.

[73] Assignee: Ciba-Geigy Corporation, Ardsley, N.Y.

[21] Appl. No.: 864,072

[22] Filed: Dec. 23, 1977

Related U.S. Application Data

[63] Continuation of Ser. No. 652,367, Jan. 26, 1976, abandoned.

[51] Int. Cl.² .............................................. C07C 91/04
[52] U.S. Cl. ............................ 260/584 R; 260/584 C; 260/609 R; 560/103; 560/110; 560/165; 560/251; 528/70
[58] Field of Search ........... 260/609 R, 584 R, 584 B, 260/584 C

[56] References Cited

U.S. PATENT DOCUMENTS

| | | | |
|---|---|---|---|
| 2,911,390 | 11/1959 | Smith | 260/77.5 |
| 3,413,271 | 11/1968 | Weesner | 260/77.5 |
| 3,547,894 | 12/1970 | Smeltz | 260/77.5 |
| 3,759,874 | 9/1973 | Gresham | 260/77.5 |
| 3,883,596 | 5/1975 | Hager et al. | 260/609 R |
| 3,906,049 | 9/1975 | Hager et al. | 260/609 R |
| 3,914,319 | 10/1975 | Dear et al. | 260/609 R |
| 3,935,277 | 1/1976 | Dear et al. | 260/609 R |
| 4,001,305 | 1/1977 | Dear et al. | 260/609 R |

Primary Examiner—Donald G. Daus
Assistant Examiner—M. C. Eakin
Attorney, Agent, or Firm—Michael W. Glynn

[57] ABSTRACT

Polyfluoroalkylthio alcohols and esters thereof are disclosed with utility as intermediates for the synthesis of fluorochemicals with low free surface energies having oil and water repellent properties. The novel alcohols and esters are obtained by a free radical catalyzed addition of polyfluoroalkylthiols to acetylenic alcohols or esters thereof. The alcohols are employed in preparation of fluorine containing polyurethanes which are useful as finishes to provide oil and water repellency to textiles and as additives to plastics to provide mold release and other desirable properties.

9 Claims, No Drawings

POLYFLUOROALKYLTHIO ALCOHOLS, ESTERS AND USEFUL COMPOSITIONS THEREFROM

This is a continuation of application Ser. No. 652,367 filed on Jan. 26, 1976 now abandoned.

The instant invention is directed to novel perfluoroalkyl-group containing alcohols and ester derivatives thereof, which are useful as intermediates for the synthesis of fluorochemical compounds which possess low free surface energies and provide oil and water repellency. The novel alcohols and esters are of the following structure (Formula I):

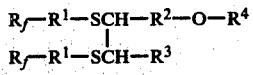

wherein
$R_f$ is $C_pF_{2p+1}$ or $C_qF_{2q}OC_pF_{2p+1}$, where p is 1 to 18 and preferably 6 to 12, and q is 2 to 8;
$R^1$ is $C_nH_{2n}$, $C_nH_{2n}SC_nH_{2n}$, $C_nH_{2n}OC_nH_{2n}$ or $C_nH_{2n}NR^5C_nH_{2n}$, where n is 1 to 12 and $R^5$ is H or alkyl with 1 to 6 carbons;
$R^3$ is H or $C_nH_{2n+1}$ where n is 1 to 12;
$R^2$ is $C_mH_{2m}$ or $C_mH_{2m}(OC_kH_{2k})_r$, where m is 0 to 12, k is 2 to 6 and r is 1 to 30; and
$R^4$ is H or

where $R^6$ is alkyl of 1 to 24 carbon atoms, aryl of 6 to 24 carbon atoms (particularly phenyl and naphthyl and lower-alkyl substituted phenyl and naphthyl) or aralkyl of 7 to 24 carbons (particularly benzyl and lower alkyl substituted benzyl).

The novel alcohols and esters of Formula I are obtained by a free radical catalyzed addition reaction of polyfluoroalkyl thiols of Formula II to acetylenic alcohols or esters of Formula III.

II $R_f\text{-}R^1\text{-}SH$

III $R^3\text{-}C\equiv C\text{-}R^2\text{-}O\text{-}R^4$ wherein
$R_f$, $R^1$, $R^2$, $R^3$ and $R^4$ are as defined above.

The formation of the alcohols and esters proceeds via the intermediate IVa and b, which may be present as by-products in the alcohols and esters of Formula I as discussed later:

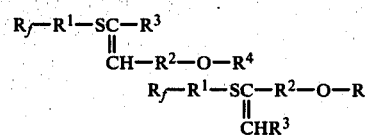

Suitable starting thiols of Formula II are well documented in the prior art. Illustratively, thiols of the formula $R_f\text{-}R^1\text{-}SH$ have been described in a number of U.S. Pat. Nos. including 2,894,991; 2,961,470; 2,965,677; 3,088,849; 3,172,190; 3,544,663 and 3,655,732.

The preferred thiols are most conveniently made by treatment of an appropriate iodide with thiourea which is followed by hydrolysis of the intermediate isothiouronium iodide:

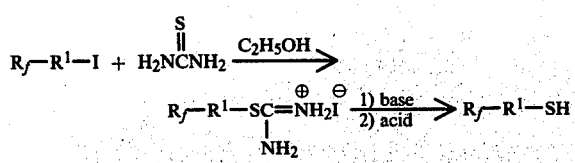

A process of this type is described in U.S. Pat. No. 3,544,663 and is applicable to straight and branched chain iodides. In Australian 36868/68, compounds are disclosed as $(CF_3)_2CFOCF_2CF_2CH_2CH_2I$ and conversion to $(CF_3)_2CFOCF_2CF_2CH_2CH_2SH$ takes place in high yield.

Of the $R_f$ thiols listed in the cited patents, the following thiols are considered most important:

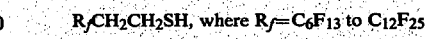
$R_fCH_2CH_2SH$, where $R_f=C_6F_{13}$ to $C_{12}F_{25}$

These $R_f$ thiols can be prepared from $R_fCH_2CH_2I$ in very high yields.

Alcohols of Formula I wherein $R^2$ is $C_mH_{2m}(OC_kH_{2k})_r$ can be made in two convenient ways. Alcohols of Formula I where $R^4$ is H may be allowed to react with suitable alkylene oxides, such as ethylene oxide, propylene oxide, etc., in the presence of acidic or basic catalysts; or the original acetylenic alcohols themselves may be similarly converted to the hydroxy alkyl esters, followed by free radical addition of the thiol $R_f\text{-}R^1\text{-}SH$.

Similarly the esters of Formula I may be made by convenient alternate routes. Alcohols of Formula I may be esterified by well-known synthetic organic methods, such as treatment of the alcohol with a carboxylic acid anhydride, an acyl halide or a carboxylic acid. Alternately, the thiols $R_f\text{-}R^1\text{-}SH$ may be added to commercially available esters represented by $R^3\text{-}C\equiv C\text{-}R^2\text{-}O\text{-}R^4$, where $R^1$, $R^2$, $R^3$ and $R^4$ are as previously defined.

As previously mentioned, suitable starting materials in the synthetis include acetylenic alcohols, and esters thereof.

Acetylenic alcohols of Formula III which are commercially available include:
propargyl alcohol
2-butyn-1-ol
3-butyn-1-ol
3-butyn-2-ol
2-methyl-3-butyn-2-ol
3,4-dimethyl-1-pentyn-3-ol
3-ethyl-1-pentyn-3-ol
2-methyl-3-pentyn-2-ol
3-methyl-1-pentyn-3-ol
4-methyl-1-pentyn-3-ol
1-pentyn-3-ol
2-pentyn-1-ol
3-pentyn-1-ol
3-pentyn-2-ol
4-pentyn-1-ol
4-pentyn-2-ol
3-isopropyl-3-hydroxy-4-methyl-1-pentyne
3,4,4-trimethyl-1-pentyn-3-ol
3-isobutyl-5-methyl-3-hydroxy-1-hexyne
3,5-dimethyl-1-hexyn-3-ol
4-ethyl-1-hexyn-3-ol
1-hexyn-3-ol
2-hexyn-1-ol 3-hexyn-1-ol
3-hexyn-2-ol
4-hexyn-2-ol
5-hexyn-1-ol
5-hexyn-3-ol
2-methyl-3-hexyn-2-ol
3-methyl-1-hexyn-3-ol
3-methyl-4-hexyn-3-ol 3,6-dimethyl-1-heptyn-3-ol
3-ethyl-1-heptyn-3-ol
3-ethyl-5-methyl-1-heptyn-3-ol
1-heptyn-3-ol
2-heptyn-1-ol
3-pentyn-1-ol
4-heptyn-2-ol
5-heptyn-3-ol
3-methyl-4-heptyn-3-ol
4-methyl-1-heptyn-3-ol
4-methyl-1-heptyn-4-ol
4-ethyl-1-octyn-3-ol
3-methyl-1-nonyn-3-ol
2-nonyn-1-ol
3-nonyn-1-ol
5-nonyn-3-ol
2-decyn-1-ol
3-decyn-1-ol
3-methyl-1-dodecyn-3-ol Commercially available acetylenic esters of Formula III include:
propargyl acetate
propargyl propionate In addition of $R_f$-thiols of Formula II to acetylenic alcohols or esters of Formula III via the intermediate IV is considered consistent with the general pathway for the free radical addition of thiols to acetylenes (Acetylenes and Allenes; T. F. Rutledge, Reinhold Book Corporation, 1969, page 142). That the addition of the thiol to the triple bond is a stepwise reaction proceeding through the intermediate IV, can be shown by reacting the thiol with an excess of the acetylenic alcohols or esters, which process gives Formula IV intermediates in high yields as exemplified later.

The free radical catalyzed addition of $R_f$-thiols of Formula II to acetylenic alcohols or esters of Formula III can be accomplished by employing reaction conditions and initiators as recommended in the literature for the addition of non-fluorine containing thiols to acetylenic alcohols and esters. (Chemistry of Acetylenes by H. G. Viehe, pages 342–346, Marcel Dekker, Inc., New York 1969 and Acetylenes and Allenes by T. F. Rutledge, pages 142–144, Rheinhold Book Corporation, 1969). Initiators which may be employed for the addition reaction, in quantities ranging from 0.1 to 40 mole percent, include peroxides and azo compounds which may be added batchwise or continuously to the reaction mixtures.

Peroxides which may be used include alkyl peroxides, such as di-t-butyl peroxide, isopropyl peroxide, di-t-amyl peroxide and dicumyl peroxide; acyl peroxides, including benzoyl peroxide, lauroyl peroxide, butyryl peroxide and succinoyl peroxide; hydroperoxides, including cumene hydroperoxide and t-butyl hydroperoxide; ketone peroxides exemplified by methyl ethyl ketone peroxide; and peresters and peroxycarbonates such as t-butyl peroxycarbonate and t-butyl peracetate.

Azo compounds which may be used include azobisisobutyronitrile; 2-t-butylazo-2-cyano-4-methoxy-4-methyl pentane; 4,4'-azobis(4-cyano valeric acid); 2-t-butylazo-2-cyano-4-methyl pentane; 4-t-butylazo-4-cyano valeric acid; ethylene bis(4-t-butylazo-4-cyano valerate); 2-(t-butylazo)isobutyronitrile; 2-t-butylazo-2-cyanobutane; 1-cyano-1-(t-butylazo)-cyclohexane; t-butylazo formamide and 2-t-butylazo-2-methoxy-4-methyl pentane.

It is also possible to carry out the reaction in the absence of a catalyst at higher temperatures such as 150° to 200° C., while in the presence of catalysts, reaction temperatures from 40° to 150° C. are employed. It is further possible to utilize ultraviolet radiation alone or in combination with free radical initiators to accomplish the reaction and under these conditions the reaction temperatures may range from 10° to 150° C.

Other peroxide or azo initiators useful for the outlined addition reaction are listed in Polymer Handbook, Ed. by T. Brandrup and E. H. Immergut pages II-3 to II-51; Interscience Publishers, New York, 1966.

The reaction can furthermore be carried out in bulk or in a suitable medium which acts to disperse or dissolve the reactants. The bulk reaction, without a solvent medium, is usually the preferred one.

Acceptable solvents include ketones, such as acetone, methyl ethyl ketone and methylisobutyl ketone; esters such as ethyl acetate, butyl acetate, 2-ethylhexyl acetate; hydrocarbons such as hexane, heptane, octane and higher homologs, cyclohexane, benzene, toluene, xylene or blends of aliphatic, cycloaliphatic and aromatic hydrocarbons; alcohols such as ethanol, n-propanol, isopropanol, t-butanol and methyl cellosolve; ethers, both aliphatic and alicyclic including di-n-propyl ether, di-butyl ether and tetrahydrofuran. In addition, chlorinated solvents such as di-chloroethyl ether, ethylene dichloride, perchloroethylene and carbon tetrachloride can be employed.

It was found, however, that when the addition reaction of $R_f$-thiols to acetylenic alcohols and esters was carried out utilizing procedures described in the literature for the addition of non-fluorinated thiols to acetylenic compounds very poor results were obtained.

While the novel alcohols and esters of type I were obtained utilizing the previously listed conditions, catalysts and solvents, the yield proved to be low and the formation of mono adducts of Formula IV and of disulfides of the type $(R_f-R^1-S)_2$ undesirably high. Reaction conditions as described by A. T. Blomquist and J. Wolinsky, J. Org. Chemistry, 23, (1958) utilizing UV radiation and peroxides at room temperature with reaction times from 1 to 4 weeks were unacceptable from a commercial standpoint.

It was found, however, that the novel alcohols and esters of type I could be prepared in 90 to 100% yields and with less than 2% of the mono adducts of Formula IV if the reaction was carried out employing specific catalysts in combination with or without specific solvents and specific molar ratios of $R_f$-thiols of Formula II and alcohols and esters of Formula III.

These results were obtained when (a) a solvent-free reaction was carried out and (b) azo componds (and preferably azo bisisobutyronitrile for reasons of economy and availability) in amounts of 0.5 to 20 mole % were employed as initiators at temperatures ranging from 60° to 80° and preferably 75° C., and (c) employing a molar ratio of $R_f$-thiol (II) to acetylenic alcohol or ester (III) of 2.0:1 up to 2.5:1. If the addition reaction is carried out under these conditions the reaction is terminated, (usually after 6 to 10 hours using azobisisotrityronitrile at 75° C.) when 85 to 95% of the $R_f$-thiol II has been converted to the novel $R_f$-alcohols and esters of Formula I. While conversion is in the range of 60 to 95% and usually 90%, the overall yield of the novel $R_f$-alcohols, diols and esters of Formula I ranges from 90 to 98% (based on the expensive $R_f$-thiol) due to the fact that the excess of thiol can be recovered and recycled.

Since the diaddition products are generally insoluble in aliphatic and aromatic hydrocarbon solvents, whereas the thiols themselves are completely miscible with these materials, the unreacted thiol is readily recovered by washing of the product with a suitable hydrocarbon such as heptane or benzene. Alternately, the thiols may be recovered by passing the crude product through a molecular distillation apparatus under conditions such that the diaddition products pass through while the thiols are volatilized, then subsequently condensed and recovered.

While the process carried out in bulk is the preferred process, it is nevertheless understood that heptane and other aliphatic hydrocarbons, such as hexane, actane, decane, etc., and commercial hydrocarbon mixtures may also be used. In addition a process utilizing aromatic hydrocarbons solvents, such as benzene, toluene or xylene may also be applied. Other solvents, already described, are less desirable, but still allow formation of the claimed products.

The alcohols of Formula I can be used to make $R_f$-containing urethane compositions. These urethane compositions have extremely low free surface energies and therefore, possess oil and water repellent properties, as well as mold release and other properties associated with low free surface energy. It should be noted that the urethane compositions of this invention are characterized by the presence of two perfluoroalkylthio groups on adjacent carbon atoms, a characteristic which provides improved oil and water repellent properties over the fluorinated urethane compositions of the prior art. Using the $R_f$-compounds and compositions described herein, it is possible to manufacture molds that display the excellent release properties characteristic of the silicone polymers.

In addition, the compounds where $R^2$ is $C_mH_{2m}(OC_kH_{2k})_r$ are useful as nonionic surfactants, especially where r is an integer from about 5 to about 30.

The esters, where $R^4$ is acyl, are useful as additives to synthetic and natural polymers to reduce the surface energy and to provide mold release characteristics.

The alcohols, where $R^4$ is hydrogen can be used in the preparation of a variety of condensation products such as polyesters, p-lyamides, polycarbonates, polyurethanes and the like. The polyurethanes are particularly preferred.

As used herein the term "urethane composition" means compounds and compositions which contain the characteristic

linkage and at least one $R_f$-containing group of formula

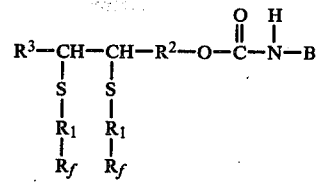

where $R_f$, $R_1$, $R_2$ and $R_3$ are as previously described, and B is an organic isocyanate residue.

Preferred urethane compositions include those where $R_f$, $R_1$, $R_2$ and $R_3$ have the configurations previously described as being preferred.

The $R_f$-alcohols can be used to make a wide variety of urethane intermediates and end products including hydroxyl and isocyanate-terminated prepolymers, low molecular weight urethane compositions useful to render plastics soil repellent, and high molecular weight compositions useful as elastomers, foams, paints and varnishes, and textile treating compositions. It is also possible to modify these $R_f$-containing urethane compositions so that they are water soluble or self-emulsifiable, a property that is particularly useful in connection with the textile treating compositions.

Polyurethane elastomers generally have remarkable resistance to most solvents including gasoline, aliphatic hydrocarbons and, to some degree, aromatic hydrocarbons. They also exhibit excellent abrasion resistance. By inclusion of the $R_f$-alcohol in an elastomer formulation, it is possible to increase the solvent resistance of urethane elastomers. The elastomers generally involve the reaction product of a diisocyanate, a linear long chain diol and a low molecular weight chain extender such as a glycol, diamine or polyol. Today, elastomers are generally prepared by a prepolymer technique whereby a diisocyanate is reacted with a hydroxyl-terminated polyester or polyether to form an isocyanate-terminated prepolymer. This prepolymer is then further reacted (chain extended) with a glycol, diamine or polyfunctional polyol (e.g. trimethylolpropane). Following the chain extension step, the liquid material solidifies and is removed from a mold and cured at elevated temperatures.

Urethane foams are usually prepared from diisocyanates and hydroxyl-terminated polyethers or polyesters. Linear or slightly branched polymers are used to provide flexible foams while more highly branched polymers produce rigid foams. Foaming is often accomplished by including water in the system, the reaction between isocyanate and water providing carbon dioxide for foaming. For rigid foams a low-boiling liquid such as trichlorofluoromethane has been used as a blowing agent.

Appropriate selection of catalysts, stabilizers, surfactants and other additives controls the foam formation, cell size and type, density, cure and the like. By incorporating the $R_f$-alcohol into urethane foams, especially molded foams, it is possible to achieve improved mold release properties in rigid, semi-rigid and flexible foams. It is also possible to improve the water and solvent resistance of foams used as insulation.

Incorporation of the $R_f$-alcohols into polyurethane coatings such as paints and varnishes improves the water and solvent resistance thereof. Widely used systems include the two-component coatings wherein a non-volatile isocyanate derived from the reaction of tolylene diisocyanate with a polyol such as trimethylolpropane, is reacted with a polyfunctional polyester. Another system in use involves the one-component polyurethane coatings which are based on stable isocyanate-terminated prepolymers obtained from a diisocyanate such as tolylene diisocyanate and a polyfunctional polyether. Such coatings dry by the reaction of the free isocyanate groups with water or atmospheric moisture. The reaction proceeds through the unstable carbamic acid, with $CO_2$ being eliminated, to give primary amine groups which further react with isocyanate groups to form ureas.

Treatment of a textile with a fluorine-containing composition, notably a fluorine-containing polyurethane, provides oil and water-repellent characteristics thereto. Polyurethane compositions containing the residue of the $R_f$-alcohol display improved oil and water repellence on textile substrates.

Of higher molecular weight urethane compositions, linear polymers, obtained by reacting a glycol with an organic diisocyanate, those having terminal structural units of formula

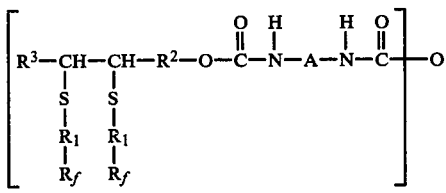

where $R_f$, $R_1$, $R_2$, and $R_3$ are as previously defined and A is a divalent organic radical, preferably alkylene of 2 to 16 carbon atoms, unsubstituted or substituted phenylene or naphthylene or unsubstituted or substituted biphenylene or bisphenylene are useful as plastics, fibers, coatings and the like.

Most urethane compositions that are used commercially to any great extent are copolymers that contain only a relatively small number of urethane linkages. These copolymers are prepared from a variety of segments, typically based on polyethers and polyesters and can have a molecular weight of from 200 to 10,000, generally from about 200 to about 4,000. By the inclusion of an appropriate amount of $R_f$-alcohol in the starting materials, it is possible to prepare prepolymers that, when incorporated as part of a urethane composition favorably affect the properties thereof. It is similarly possible to incorporate a desired amount of $R_f$-alcohol into the reaction mixture of a conventional prepolymer and an isocyanate.

The $R_f$-containing prepolymers can be hydroxy-terminated or isocyanate-terminated and, as indicated, can have a molecular weight as high as 10,000 although a molecular weight of 200 to about 4,000 is more usual.

Hydroxy-terminated prepolymers can be prepared by reacting an excess of a polyhydroxy component with a polyfunctional hydroxy-reactive component such as a polyisocyanate; an isocyanate-terminated prepolymer; a polybasic carboxylic acid, anhydride or acyl halide; phosgene; or a bischloroformate.

The polyhydroxy component can be a polyol, an $R_f$-glycol, a polyether, a polyester, an $R_f$-containing polyether, an $R_f$-containing polyester or mixture thereof.

The polyols are well-known in the urethane art and include

Ethylene glycol
1,3-propanediol
1,4-butanediol
1,5-pentanediol
1,6-hexanediol
1,9-nonanodiol
1,10-decanediol
di-, tri-, tetra- and pentaethylene glycol
bis(4-hydroxybutyl) ether
bis(2-hydroxyethyl) thioether
bis(4-hydroxybutyl) thioether
1,4-bis(3-hydroxypropyl) benzene
glycerol
trimethylolpropane
1,2,6-hexanetriol
sorbitol
mamitol
pentaerythritol,
2-ethyl-1,3-butylene glycol
octanethylene glycol
2-ethyl-1,3-hexanediol
dodecamethylene glycol
tetradecamethylene glycol
hexadecamethylene glycol
octadecamethylene glycol The polyol can also contain cycloaliphatic groups, e.g. 1,4-cyclohexane-diol, 1,4-bis(hydroxymethyl) cyclohexane, 4,4'-dihydroxyl-1,1'-dicyclohexyl and the like. If desired, mixtures of polyols can be used.

Polyols in addition to those described above, that are considered especially useful, are those containing tertiary nitrogen atoms which can be quaternized with acids, thereby converting a water-insoluble urethane composition into one that is water soluble or emulsifiable. Generally, an isocyanate-terminated prepolymer having a molecular weight of 200 to 10,000, preferably 400 to 4,000, is reacted with a difunctional tertiary amine to provide a segmented polymer containing tertiary nitrogen atoms. The nitrogen atoms can be quaternized, for example, by alkylation with methyl chloride or dimethyl sulfate to yield a composition that in polar media yields a dispersion in water. The polyammonium polyurethane compositions are obtained even more readily by neutralization of the basic polyurethane composition in a polar organic solvent such as acetone, methyl ethyl ketone, tetrahydrofuran, with a strong (HCl) or preferably weak (pK>4) acid such as the $C_2$-$C_9$ alkanoic acids. Acetic acid is especially preferred because the acetic acid evaporates with the water on drying to leave the water-insoluble hydrophobic starting polyurethane composition.

The neutralized polyurethane composition in a polar solvent spontaneously forms a dispersion when water is stirred in. The solvent can thereafter be distilled off to give a solvent-free latex whose film-forming qualities are comparable to those of the organic solution.

In a convenient mode of preparing the water-dispersible basic polyurethane compositions, a polyester or polyether diol is reacted in a non-reactive polar solvent such as acetone, methyl ethyl ketone, tetrahydrofuran and the like, with an excess of a diisocyanate such as tolylene diisocyanate or, preferably an aliphatic diisocyanate which tends to give non-yellowing urethanes such as dimer acid derived diisocyanate (DDI, commercially available from Quaker Oats Company) or another diisocyanate which is described herein as providing non-yellowing urethanes, and the prepolymer partially chain extended with an alkyl diethanolamine to yield a urethane composition containing tertiary amino groups. The urethane composition can then be acidified with a solution of aqueous weak acid (pK>4) such as acetic acid; the concentration of acid is not critical. An emulsion immediately forms when this composition is added to water.

The polyurethane compositions can contain from as little as 5 to 800 milliequivalents of ammonium groups per 100 grams of polyurethane composition, preferably from about 50 to about 500 milliequivalents of ammonium groups per 100 grams.

Some useful polyols containing tertiary nitrogen atoms can be represented by the formula

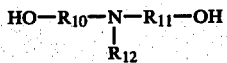

where
$R_{10}$ and $R_{11}$ are alkyl of 2 to 4 carbon atoms or a group of formula

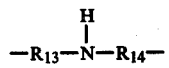

where
$R_{13}$ and $R_{14}$ are alkyl of 2 to 4 carbon atoms
$R_{12}$ is alkyl of 1 to 18 carbon atoms, cyclohexyl, tolyl xylyl, naphthyl, or with the nitrogen atom forms piperazyl or pyridyl.

Useful polyols that contain tertiary nitrogen atoms include the alkoxylated aliphatic, cycloaliphatic aromatic and heterocyclic primary amines:
N-methyl-diethanolamine
N-butyl-diethanolamine
N-oleyl-diethanolamine
N-cyclohexyl-diethanolamine
N-methyl-diisopropanolamine
N-cyclohexyl-diisopropanolamine
N,N-dihydroxyethylaniline
N,N-dihydroxyethyl-m-toluidine
N,N-dihydroxyethyl-p-toluidine
N,N-dihydroxypropyl-naphthylamine
N,N-tetrahydroxyethyl-aminopyridine
dihydroxyethylpiperazine
polyethoxylated butyldiethanolamine
polypropoxylated methyldiethanolamine (molecular wt. 1000)
polypropoxylated methyldiethanolamine (molecular wt. 2000)
polyesters with tertiary amino groups
tri-2-hydroxypropyl-(1)-amine
N,N-di-n-(2:3-dihydroxypropyl)-aniline
N,N'-dimethyl-N,N'-bis-hydroxyethylhydrazine
N,N'-bis-hydroxypropylethylenediamine
N,N'-dimethyl-N,N-bis(hydroxyethyl)-ethylenediamine
N-stearyldiethanolamine
N,N'-bis(hydroxyethyl)-piperazine Useful polyethers are well-known and widely employed in urethane technology.

The polyethers are generally prepared commercially from lower alkylene oxides e.g. ethylene, propylene and butylene oxide and di- or polyfunctional alcohols. They have a molecular weight of from 400 to 5000. A list of commercially available polyethers, trade names, molecular weight range and suppliers can be found in Volume 11, Polyurethane, page 511, Encyclopedia of Polymer Science and Technology, John Wiley and Sons, Inc., 1969.

Hydroxy-terminated polyesters can be prepared from a polybasic acid, anhydride or aryl halide and a polyol, as described above and/or an $R_f$-glycol.

Useful dicarboxylic acids are those derived from a saturated aliphatic dicarboxylic acid of 2 to 18 carbon atoms or an aromtic dicarboxylic acid of 8 to 18 carbon atoms, e.g. compounds of formula $B(COOH)_2$ where B is preferably alkylene of 0–16 carbon atoms or arylene of 6 to 16 carbon atoms. Such acids include oxalic, malonic, succinic glutanic, adipic, pimelic, suberic, azelaic, sebacic, brassylic, thopsic, octadecanedioic, 1,4-cyclohexanedicarboxylic, 4,4'-dichlohexyl-1,1'-dicarboxylic, phthalic, isophthalic, terephthalic, methylphthalic, chlorophthalic, diphenyl-2,2'-dicarboxylic, diphenyl-4,4'-dicarboxylic, 1,4-naphthalene dicarboxylic, diphenylmethane-2,2'-dicarboxylic, diphenylmethane-3,3'-dicarboxylic, diphenylmethane-4,4'-dicarboxylic acid and the like.

Adipic acid and phthalic anhydride are the most common acid and anhydride. Of the polyols, the most commonly used include ethylene glycol, propylene glycol, 1,2-, 1,3- and 1,4-butylene glycol, 1,6-hexylene glycol, trimethylolpropane, glycerol 1,2,6-hexanetriol and diethylene glycol.

Useful hydroxyl-terminated polyesters can also be derived from natural castor oil and glycerol or from caprolactones and ethylene glycol. Such hydroxy-terminated polyesters have hydroxyl numbers ranging from 40 to 500 and very low acid numbers ranging from 0 to 2.

Hydroxyl-terminated polycarbonates can be obtained by reacting an excess of a polyol with phosgene.

Hydroxy-terminated polybutadienes, or butadienes-tyrenes and butadiene-acrylonitriles are useful herein, as are hydroxyl containing graft polymers of the polyetherpolyacrylonitrile type.

Any convenient isocyanate can be used to react with the $R_f$ alcohol or $R_f$-containing hydroxy-terminated prepolymer. Myriads of useful isocyanates are well-known in the art. Thus, one can use aromatic isocyanates, diisocyanates triisocyanates and polyisocyanates.

Useful aromatic diisocyanates can be represented by the formula

where
A is phenylene that is unsubstituted or substituted by one or two of alkyl of 1 to 4 carbon atoms, alkoxy of 1 to 4 carbon atoms chloro, bromo and nitro naphthylene that is unsubstituted or substituted by one or two of alkyl of 1 to 4 carbon atoms, chloro, bromo and nitro
or where
A is a group of formula

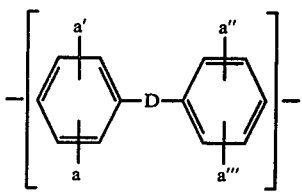

where
D is a direct bond, oxygen, methylene or ethylene and
a, a', a" and a''' each independently is hydrogen, alkyl of 1 to 4 carbon atoms alkoxy of 1 to 4 carbon atoms, chloro or bromo Aromatic triisocyanates can be represented by the formula $$B(NCO)_3$$

where
B is the benzene or toluene group.

Armoatic di- and triisocyanates as described above include -
Tolylene diisocyanate (TDI) (all isomers),
4,4'-diphenylmethane diisocyanate (MDI)
Tolidine diisocyanate
Dianisidine diisocyanate
m-Xylylene diisocyanate
p-Phenylene diisocyanate
m-Phenylene diisocyanate
1-Chloro-2,4-phenylene diisocyanate
3,3'-Dimethyl-4,4'-bisphenylene diisocyanate
3,3'Dimethyoxy-4,4'-bisphenylene diisocyanate
4,4'-Bis(2-methylisocyanatophenyl) methane
4,4'-bisphenylene diisocyanate
4,4'-Bis(2-methoxyisocyanatophenyl) methane
1-nitro-phenyl-3,5-diisocyanate
4,4'-diisocyanatodiphenyl ether
3,3'-dichloro-4,4'-diisocyanatodiphenyl ether
3,3'-dichloro,4,4'-diisocyanatodiphenyl methane
4,4'diisocyanatodibenzyl
3,3'-dimethyl-4,4'-diisocyanatodiphenyl
3,3'-dimethoxy-4,4'-diisocyanatodiphenyl
2,2'-dimethyl-4,4'-diisocyanatodiphenyl
2,2'-dichloro-5,5'-dimethoxy-4,4'-diisocyanatodiphenyl
3,3'-dichloro-4,4'-diisocyanatodiphenyl
benzene-1,2,4-triisocyanate
benzene-1,3,5-triisocyanate
benzene-1,2,3-triisocyanate
toluene 2,4,6-triisocyanate
toluene 2,3,4-triisocyanate
1,2-naphthalene diisocyanate
4-chloro-1,2-naphthalene diisocyanate
4-methyl-1,2-naphthalene diisocyanate
1,5-naphthalene diisocyanate
1,6-naphthalene diisocyanate
1,7-naphthalene diisocyanate
1,8-naphthalene diisocyanate
4-chloro-1,8-naphthalene diisocyanate
2,3-naphthalene diisocyanate
2,7-naphthalene diisocyanate
1,8-dinitro-2,7-naphthalene diisocyanate
1-methyl-2,4-naphthalene diisocyanate
1-methyl-5,7-naphthalene diisocyanate
6-methyl-1,3-naphthalene diisocyanate
7-methyl-1,3-naphthalene diisocyanate
polymethylene polyphenyl isocyanate and
co-products of hexamethylene diisocyanate and tolylene diisocyanate Useful aliphatic diisocyanates include those of general formula $$A(NCO)_2$$

where
A is alkylene of 2 to 16 carbon atoms.
Useful aliphatic polyisocyanates include -
1,2-ethane diisocyanate
1,3-propane diisocyanate
1,4-butane diisocyanate
2-chloropropane-1,3-diisocyanate
pentamethylene diisocyanate
propylene-1,2-diisocyanate
1,6-hexane diisocyanate
1,8-octane diisocyanate
1,10-decane diisocyanate
1,12-dodecane diisocyanate
1,16-hexandecane diisocyanate and
other aliphatic diisocyanates such as
1,3-cyclohexane diisocyanate
1,4-cyclohexane diisocyanate
cyclohexane triisocyanate diisocyanate
4,4'-methylene bis(cyclohexyl) isocyanate Additionally, the following diisocyanates are particularly preferred because urethane compositions made therefrom tend to be non-yellowing:
1,6-hexamethylenediisocyanate (HDI)
2,2,4- and 2,4,4-trimethylhexamethylenediisocyanate (TMDI)
dimeracid derived diisocyanate (DDI) obtained from dimerized fatty acids, such as
linoleic acid 4,4'-dicyclohexylmethane diisocyanate (hydrogenated MDI)
isophorone diisocyanate
3-isocyanatomethyl-3,5,5-trimethylcyclohexylisocyanate
lysine methyl ester diisocyanate (LDIM)
bis(2-isocyanatoethyl) fumerate (FDI)
bis(2-isocyanatoethyl) carbonate Other useful isocyanates include polyisocyanates, particularly triisocyanates which are readily obtained by the reaction of an excess of the corresponding diisocyanate with water according to the following equation:

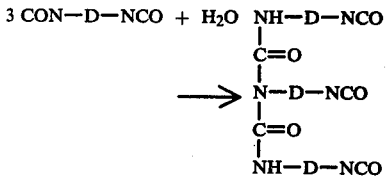

where
D is the residue of a diisocyanate as described above; additional polyisocyanates include polymethylene polyphenylisocyanate (PAPI) and tris-(isocyanatophenyl) thiophosphate (Desmodur R/).

In addition to the polyisocyanates, useful urethane compositions can be obtained from the aliphatic and aromatic monoisocyanates. The low molecular weight urethane compositions obtained by reacting an $R_f$-alcohol with a monoisocyanate are useful to impart soil and mold-release properties to a variety of natural and synthetic polymers.

Some useful aromatic monoisocyanates include -
2-fluorophenyl isocyanate
3-fluorophenyl isocyanate
4-fluorophenyl isocyanate
m-fluorosulfonylphenyl isocyanate
trans-2-phenylcyclopropyl isocyanate
m-tolyl isocyanate
p-tolyl isocyanate
$\alpha,\alpha,\alpha$-trifluoro-o-tolyl isocyanate
$\alpha,\alpha,\alpha$-trifluoro-m-tolyl isocyanate
p-bromophenyl isocyanate
2,5-dimethylphenyl isocyanate
o-ethoxyphenyl isocyanate
p-ethoxyphenyl isocyanate
o-methoxyphenyl isocyanate
m-methoxyphenyl isocyanate
p-methoxyphenyl isocyanate
l-naphthyl isocyanate
o-nitrophenyl isocyanate
m-nitrophenyl isocyanate
p-nitrophenyl isocyanate
p-phenylazophenyl isocyanate
o-tolyl isocyanate Useful aliphatic monoisocyanates include such alkyl isocyanates of 1 to 16 carbon atoms as
methyl isocyanate
ethyl isocyanate
n-propyl isocyanate
n-butyl isocyanate
t-butyl isocyanate
hexyl isocyanate
octyl isocyanate
dodecyl isocyanate
octadecyl isocyanate
hexadecyl isocyanate and mixtures thereof, as well as cyclohexyl isocyanate.

Isocyanate-terminated prepolymers typically having a molecular weight of from 200 to about 4000 can be prepared by reacting an excess of an isocyanate component with a polyhydroxy component. The isocyanate component can be a diisocyanate or polyisocyanate as previously described or can be a low molecular weight isocyanate-terminated prepolymer.

The reaction between the isocyanate component and the hydroxyl component can be carried out in bulk, i.e., without solvent, or in the presence of non-reactive, anhydrous, organic solvents. Solvent media in which the reaction can be carried out include ketones, such as acetone, methyl ether ketone and methylisobutyl ketone; esters such as ethyl acetate, butylacetate, 2-ethylhexyl acetate; hydrocarbons such as hexane, haptane, octane and higher homologs, cyclohexane, benzene, toluene, xylene or blends of aliphatic, cycloaliphatic and aromatic hydrocarbons. It is also possible to employ ethers, both aliphatic and alicyclic including di-n-propyl ether, di-butyl ether, tetrahydrofuran and the diethers of polyalkylene oxides. In addition, chlorinated solvents such as dichloroethyl ether, ethylene dichloride, perchloroethylene and carbon tetrachloride can be used.

Among the solvents listed, the water miscible solvents such as acetone and methyl ethyl ketone are most important since they allow conversion of $R_f$-urethanes into water soluble $R_f$-urethanes as previously described.

In all cases, the solvents should be anhydrous to avoid area formation.

The reaction can, if desired, be catalyzed and those catalysts conventionally employed in the urethane art are useful herein. Useful catalysts fall principally in two groups.

(a) amino compounds and other bases:
triethylamine and other trialkylamines
triethylenediamine
1,4-dlaza-2,2,2-bicyclocetane
N-(lower) alkyl morpholines
N,N,N',N'-tetra-methylethelenediamine
N,N,N',N'-tetramethyl-1,3-butanediamine
N,N'-substituted piperazines
dialkylalkanolamines
benzyltrimethylammonium chloride (b) organometallic and inorganic compounds:
cobalt naphthenate
stannous chloride
stannous octoate
stannous oleate
dimethyl tin dichloride
di-n-butyltin dilaurlmercaptide
tetra-n-butyl tin
trimethyl-tin hydroxide
di-n-butyltindilaurate Such catalysts may be used singly or in combination with each other. Beneficial synergistic catalysis may occur when combinations are used.

While it is possible to carry out the reaction without the use of a catalyst, it is preferable for reasons of economy and to assure a complete reaction, to utilize one or more catalysts as listed in amounts ranging from 0.001 to 1% based on the weight of the reactants. It is similarly advantagous to carry out the urethane synthesis at elevated temperature, usually between room temperature and 120° C. and preferably at 60° to 80° C. to obtain a complete reaction between 0.5 to 8 hours reaction time.

The reaction can be easily followed by titration of the isocyanate group or by IR analysis.

The determination of the critical surface tension ($\gamma_c$) in dynes per centimeter shows that the free surface energy of a polyurethane is lowered if the novel $R_f$-alcohols are incorporated into the urethane chain.

The critical surface tensions ($\gamma_c$) are determined by contact angle measurements as described by W. Zisman, *Contact Anles*, Advances in Chemistry, No. 43, ACS Publications, Washington, D.C., 1964.

The usefulness of the polyurethane compositions is, however, conveniently shown by measuring the oil, water and soil repellency ratings of substrates such as fabrics, paper, leather, etc. which are treated with solutions or emulsions of the novel urethane compositions.

As already indicated, the urethane compositions of the invention are highly effective for imparting oil and water repellent properties to substrates to which they are applied and coatings of these polymers may be prepared by any of the well-known techniques. When prepared by bulk or suspension polymerization techniques, these urethane compositions can be applied, for example, from a dilute solution in suitable a solvent such as the fluoroalkanes, fluorochloroalkanes, fluoroalkyl substituted aromatics, alkylesters of perfluoroalkanoic acids, chlorinated alkanes or aromatics, hydrocarbon aromatics, ketones, esters and others. Concentrations of the fluorinated polymer in the solvent can be adjusted to provide an amount of urethane composition deposited on the substrate sufficient to provide oil and water repellency. This amounts typically to a deposit of from 0.01 to 10%, preferably from 0.1 to 1%, of urethane composition, based on the weight of substrate. If the urethane composition is obtained as an aqueous latex or emulsion, the system can be diluted with water or other appropriate diluent to similarly provide an amount of urethane ranging from 0.01 to 10% of the weight of substrate deposited thereon.

The urethane solution or latex may be applied by any of the known techniques such as by dipping, spraying, brushing, padding, roll coating or by any desired combination of such techniques. The optimum method of application will depend principally on the type of substrate being coated.

Coatings of the urethane compositions of the invention may be applied to any desired substrate, porous or non-porous. They are particularly suited for application to porous materials such as textiles, leather, paper, wood, masonry, unglazed porcelain and the like to provide valuable oil and water repellency properties. However, they may also be applied to non-porous materials such as metals, plastics, glass, painted surfaces and the like to provide similar oil and water repellency properties.

In the treatment of paper the urethane compositions may be present as an ingredient in a wax, starch, casein, elastomer, or wet strength resin formulation. Aqueous emulsions of the urethane compositions are especially useful in the treatment of paper. By mixing the urethane compositions in an aqueous or oil type paint formulation, it may be applied effectively to unpainted asbestos siding, wood, metal and masonry. In the treatment of floors and tile surfaces and like substrates, the urethane compositions may be applied by their incorporation in an emulsion or solution.

Because of the ability of the surfaces treated with these urethane compositions to withstand abrasive action, the advantages incident to the repellency to oil and water and their resistance to soiling imparted by coating them with the urethane compositions of this invention, preferred classes of articles to be treated are papers and textiles. Illustrative papers are carbonizing tissue, wallpaper, asphalt laminates, liner board, cardboard and papers derived from synthetic fibers.

For application to textile materials such as fabrics woven and non-woven, fibers, films, yarns, cut staple, thread, etc. or articles made from fabrics, fibers, films, yarns, etc. the urethane compositions of the invention are preferably prepared as aqueous latices or emulsions which are then diluted, preferably with water and applied to the textiles from pad baths which may contain other treating materials. In accordance with this technique, the fabric or the textile material is passed through the bath, passed through squeeze rolls adjusted to leave the desired amount of the latex on the fabric, dried at a temperature of about 25° to 125° C. and then cured in a curing oven at a temperature in the range of from 120° to 195° C. for 0.2 to 20 minutes. The weight of urethane composition deposited on the fabric may range from 0.01 to 10% of the weight of fabric. Preferably, very small amounts are used in the range of 0.1 to 1%, often from 0.1 to 0.5% to give high degrees of water and oil repellency. Any types of textile materials, such as cotton, wool, fiber glass, silk, regenerated cellulose, cellulose esters, cellulose ethers, polyesters, polyamides, polyolefins, polyacrylonitrile, polyacrylic esters, inorganic fibers, etc. either alone or blended in any combination may be successfully coated with the urethane compositions of the invention. The resulting textile material will be found to be repellent to water and oil, and the textile material will retain its resistance to such agents even after many launderings and dry cleanings.

It will be often advantageous to use the urethane compositions of the invention in combination with conventional finishes, such as mildew preventatives, moth resisting agents, crease resistant resins, lubricants, softeners, fat liquors, sizes, flame retardants, antistatic agents, dye fixatives and water repellents.

The invention described above is illustrated by the following Examples, wherein temperature is given in degrees Celsius and nuclear magnetic resonance data is given in parts per million (ppm) referred to tetramethylsilane.

EXAMPLE 1

2,3-Bis(1,1,2,2-Tetrahydroperfluorodecylthio)propan-1-ol

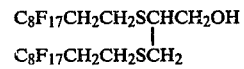

1,1,2,2-Tetrahydroperfluorodecanethiol (35.0 g; 0.073 mole) and propargyl alcohol (2.0g; 0.036 mole) were placed in a Fischer-Porter reaction tube with just enough 2-butanone to effect solution (approx. 7 ml.) The pale yellow solution was deoxygenated with nitrogen and 150 mg. azobisisbutyronitrile (ABN) was added. A magnetic stirring bar was placed in the tube, which was closed and heated at 70°–75° for 20 hours. The solution was stirred at all times. After cooling, all solvent was removed by evaporation under reduced pressure, to leave a white crystalline material. The crude material was pumped at 35° and 0.2 mm Hg to remove any unreacted thiol and propargyl alcohol. After recrystallization from benzene, the final product weighed 35.3 g and melted at 83°–84°. Yield=96.5%. Ir showed an OH stretching frequency at 3300 cm$^{-1}$. An nmr spectrum was consistent with the structure and showed the following signals:

$$2.1\text{–}3.1 \text{ ppm} \quad -CH_2CH_2SCH_2 \quad (11 \text{ H});$$
$$-CH_2CH_2SCH-$$
$$3.75 \text{ ppm} \quad -OCH_2 \text{ (2H)} \quad 4.4 \text{ ppm} \quad -OH \text{ (1H)}$$

Analysis for $C_{23}H_{14}F_{34}S_{20}$: Calculated: C, 27.18; H, 1.39; F, 63.55; Found: C, 27.54; H, 1.36; F, 62.63.

EXAMPLE 2

2,3-(Bis(1,1,2,2-Tetrahydroperfluoroctylthio)propan-1-ol

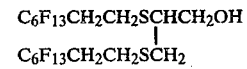

In a 250 ml three-neck flask, 1,1,2,2-tetrahydroperfuloroctanethiol (100 g; 0.263 mole) was mixed with propargyl alcohol (7.37 g; 0.131 mole) and 100 ml heptane was added. The mixture was warmed to 75° (solution was complete by 50°) with stirring and nine equal portions (90 mg. each) of azobisisobutyronitrile (ABN) catalyst was added over a 3 hour period. Stirring and heating were continued overnight. Upon cooling to room temperature two layers formed. The upper layer of heptane was separated and from this 6.4 g of unreacted thiol was recovered. The lower layer was crude product. Distillation of this layer gave a further 8.2g unreacted thiol and 64.5 g of product, boiling 160°–162° at 0.1 mm Hg. This slowly set to a waxy solid. The infrared spectrum was consistent with the structure. In particular an O–H stretching frequently at 3300 cm$^{-1}$ was present.

Analysis $C_{19}H_{14}F_{26}OS_2$: Calculated: C, 27.95; H, 1.73; F, 60.50; Found: C, 27.81; H, 1.68; F, 60.44.

EXAMPLE 3

2,3-Bis(1,1,2,2-Tetrahydroperfluoralkylthio)propan-1-ol

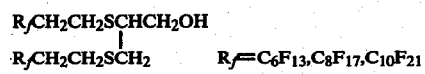

1,1,2,2-Tetrahydroperfluoroalkanethiol, a mixture of $C_6F_{13}CH_2CH_2SH$ (23.4%), $C_8F_{17}CH_2CH_2SH$ (49.1%), $C_{10}F_{21}CH_2CH_2SH$ (25.1%) and unknowns (2.5%) (300 g; 0.62 mole), and propargyl alcohol (17.4 g; 0.31 mole) were added to 600 ml heptane in a 2-liter 3-neck flask (Morton type). The material was warmed to effect solution and then stirred at 75° while catalyst azobisisobutyronitrile (ABN) was added in nine portions of 226 mg each at 20 minute intervals. The reaction mixture was stirred for 18 hours at 75°, then allowed to cool. Filtration and washing with 3×100 ml cold heptane gave 238.9 g product as a white solid m.p. 67°–79° (75.3% conversion. Combination of the filtrateland washings followed by careful evaporation allowed the recovery of 65.7 g unreacted thiol (20.7%) giving an overall yield of 96%. The identity of the product was confirmed by infrared spectroscopy showing an O–H stretching frequency at 3365 cm$^{-1}$. Gas chromatography showed the presence of five dialkyl propanols, namely, the $C_6F_{13}$, $C_6F_{13}$; $C_6F_{13}$, $C_8F_{17}$; $C_6F_{13}$, $C_{10}F_{21}$ and $C_8F_{17}$;$C_8F_{17}$; $C_8F_{17}$, $C_{10}F_{21}$ and $C_{10}F_{21}$, $C_{10}F_{21}$ adducts. The proton NMR was essentially identical with the compound of Example 1.

EXAMPLES 4 to 9

Table 1 summarizes further examples of the addition of 1,1,2,2-tetrahydro-perfluoroalkylenethiol to propargyl alcohol, using reaction conditions as outlined in Example 3.

EXAMPLES 4 to 9

| Ex. | $R_2CH_2CH_2SH$ | HCHCCH$_2$OH | SOLVENT | CATALYST | PRODUCT $R_fCH_2CH_2SCHCH_2OH$ $R_fCH_2CH_2SCH_2$ | RECOVERED $R_fCH_2CH_2SH$ | % CONVERSION | % YIELD |
|---|---|---|---|---|---|---|---|---|
| 4 | 35 g; 0.073m. | 2.Cg; 0.036m. | MEK 6ml. | BPO 50 mg. | 14.9g. | — | 40.7 | — |
| 5 | 30g; 0.062m. | 1.74g;0.031m. | MEK 15ml. | ABN 200 mg. | 25.5g. | 3.2g. | 80.5 | 91.2 |
| 6 | 100g; 0.21m. | 5.8g;0.104m. | MEK 15ml. | ABN 679 mg. | 92.2g. | 7.4g. | 87.0 | 94.0 |
| 7 | 100g; 0.21m. | 5.8g;0.104m. | Heptane 200 ml. | ABN 679 mg. | 77.9g. | 15 g. | 73.7 | 87.9 |
| 8 | 300g; 0.62m. | 17.2g; 0.31m. | Amsco 46 300 ml. | ABN 2.04 g. | 277.6g. | — | 84.4 | — |
| 9 | 300g; 0.62m. | 17.4g;0.31m. | Toluene 600 ml. | ABN 2.04 g. | 210.1g. | 75 g. | 66.3 | 91.3 |

MEK = 2 butanone
BPO = benzoyl peroxide
ABN = Azobisisobutyronitrile
AMSCO 46 = 42.4% paraffin
39.4% naphthenes
18.2% aromatics

EXAMPLES 10 to 17

Specific examples of additions of other available thiols to commercial acetylenic alcohols and esters are shown in Table 3. In each of a free radical catalyzed addition of 2 moles of thiol to 1 mole acetylenic alcohol is involved. The experimental procedure is as described in Example 11 a.

Table 2

| | | EXAMPLES 10 to 17 | |
|---|---|---|---|
| EXAMPLE | THIOL | ALCOHOL OR ESTER | PRODUCT |
| 10 | 2 $C_8F_{17}CH_2CH_2SH$ | + $CH_3C{\equiv}CCH_2CH_2OH$ | $C_8F_{17}CH_2CH_2SCHCH_2CH_2OH$<br>$\|$<br>$C_8F_{17}CH_2CH_2SCHCH_3$ |
| 11 | 2 $(CF_3)_2CFOCF_2CF_2CH_2CH_2SH$ | + $HC{\equiv}CCH_2OH$ | $(CF_3)_2CFOCF_2CF_2CH_2CH_2SCHCH_2OH$<br>$\|$<br>$(CF_3)_2CFCCF_2CF_2CH_2CH_2SCH_2$ |
| 12 | 2 $(CF_3)CFO(CF_2CF_2)_nCH_2CH_2SH$ | + $HC{\equiv}CCH_2OH$ | $(CF_3)_2CFO(CF_2CF_2)_nCH_2CH_2SCHCH_2OH$<br>$\|$<br>$(CF_3)_2CFO(CF_2CF_2)_nCH_2CH_2SCH_2$ |
| 13 | 2 $C_8F_{17}CH_2SH$ | + $HC{\equiv}CCH_2OH$ | $C_8F_{17}CH_2SCHCH_2OH$<br>$\|$<br>$C_8F_{17}CH_2SCH_2$ |
| 14 | 2 $C_8F_{17}(CH_2)_8SH$ | + $HC{\equiv}CCH_2OH$ | $C_8F_{17}(CH_2)_8SCHCH_2OH$<br>$\|$<br>$C_8F_{17}(CH_2)_8SCH_2$ |
| 15 | 2 $C_8F_{17}CH_2CH_2SH$ | + $CH_3CH_2C{\equiv}CCH(OH)CH_3$ | $C_8F_{17}CH_2CH_2SCHCH(OH)CH_3$<br>$\|$<br>$C_8F_{17}CH_2CH_2SCHCH_2CH_3$ |
| 16 | 2 $C_8F_{17}CH_2CH_2SH$ | + $HC{\equiv}CCH_2OCOCH_3$ | $C_8F_{17}CH_2CH_2SCHCH_2OCOCH_3$<br>$\|$<br>$C_8F_{17}CH_2CH_2SCH_2$ |

Table 2-continued

EXAMPLES 10 to 17

| EXAMPLE | THIOL | ALCOHOL OR ESTER | PRODUCT |
|---|---|---|---|
| 17 | 2 $C_8F_{17}(CH_2)_4SH$ | + HC≡CCH | $C_8F_{17}(CH_2)_4SCHCHOCOCH_3$<br>\|<br>$C_8F_{17}(CH_2)_4SCH_2$ | n = 1 average

EXAMPLE 18

3,4-Bis(1,1,2,2-Tetrahydroperfluorodecylthio)-butan-1-ol

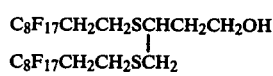

Elemental analysis:
Calculated for $C_{26}H_{20}F_{34}OS_2$: C, 29.50 H, 1.90 F, 61.02; Found: C, 30,02 H, 1.82 F, 61.78.

EXAMPLES 20-25

Other examples of the radical catalyzed addition of $R_f$-thiol to commercial acetylenic alcohols and esters, using reaction conditions as shown in example IIa are listed in Table 6

Table 3

| Ex. | Thiol | Alcohol or Ester | Product |
|---|---|---|---|
| 20 | 2 $C_8F_{17}CH_2CH_2SCH_2CH_2CH_2SH$ | + HC≡CCH$_2$OH → | $C_8F_{17}CH_2CH_2SCH_2CH_2CH_2SCHCH_2OH$<br>\|<br>$C_8F_{17}CH_2CH_2SCH_2CH_2CH_2SCH_2$ |
| 21 | 2 $C_8F_{17}CH_2CH_2SCH_2CH_2CH_2SH$ | + HC≡CCH$_2$OCOCH$_3$ → | $C_8F_{17}CH_2CH_2SCH_2CH_2CH_2SCHCH_2OCOCH_3$<br>\|<br>$C_8F_{17}CH_2CH_2SCH_2CH_2CH_2SCH_2$ |
| 22 | 2 $C_8F_{17}CH_2CH_2OCH_2CH_2CH_2SH$ | + HC≡CCH$_2$OH → | $C_8F_{17}CH_2CH_2OCH_2CH_2CH_2SCHCH_2OH$<br>\|<br>$C_8F_{17}CH_2CH_2OCH_2CH_2CH_2SCH_2$ |
| 23 | 2 $C_8F_{17}CH_2CH_2OCH_2CH_2CH_2SH$ | + HC≡CCH$_2$OCOCH$_3$ → | $C_8F_{17}CH_2CH_2OCH_2CH_2CH_2SCHCH_2OCOCH$<br>\|<br>$C_8F_{17}CH_2CH_2OCH_2CH_2CH_2SCH_2$ |
| 24 | 2 $C_8F_{17}CH_2CH_2N(CH_3)CH_2CH_2CH_2SH$ | + HC≡CCH$_2$OH → | $C_8F_{17}CH_2CH_2N(CH_3)CH_2CH_2CH_2SCHCH_2OH$<br>\|<br>$C_8F_{17}CH_2CH_2N(CH_3)CH_2CH_2CH_2SCH_2$ |
| 25 | 2 $C_8F_{17}CH_2CH_2N(CH_3)CH_2CH_2CH_2SH$ | + HC≡CCH$_2$OCOCH$_3$ → | $C_8F_{17}CH_2CH_2N(CH_3)CH_2CH_2CH_2SCHCH_2OCOCH_3$<br>\|<br>$C_8F_{17}CH_2CH_2N(CH_3)CH_2CH_2CH_2SCH_2$ |

1,1,2,2-tetrahydroperfluorodecanethiol (10 g; 0.021 mole) and 3-butyn-1-ol (0.73 g; 0.0140 mole) were heated together at 75° for 18 hours under nitrogen, using 68 mg ABN catalyst, in 20 ml heptane. The product was recrystallized from fresh heptane to give 9.5 g (88.6%) of the desired alcohol, (m.p. 57.5–59.5° C.) was a white, granular solid. The structure was confirmed by (a) infrared and (b) nmr spectroscopy and by elemental analysis which showed: (a) O-H stretching frequency at 3400 cm$^{-1}$ and (b) signals at 3.86 ppm (OCH$_2$); 1.6–3.2 ppm (OH,CH,CH$_2$)

Calculated for $C_{24}H_{16}F_{34}OS_2$: C, 27.97 H, 1.56 F 62.68; Found: C, 28.23 H, 1.34 F 62.34.

EXAMPLE 19

5,6-Bis(1,1,2,2-Tetrahydroperfluorodecylthio)hexan-1-ol

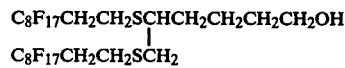

In the same manner as Example 26 reaction of 1,1,2,2-tetrahydroperfluorodecanethiol (10 g; 0.021 mole) with 5-hexyn-1-ol (1.02 g; 0.0104 mole) gave 8.3g of product alcohol (75.3% of theory) m.p. 51°–52.5°, as a white granular solid. Infrared and nmr spectra confirmed the assigned structure.

Infrared showed O-H stretching frequency at 3340 cm$^{-1}$. Nmr shows signals at 3.66 ppm (OCH$_2$) and a broad signal centered at 2.5 ppm. The —CH$_2$CH$_2$CH$_2$— chain is represented by a signal at 1.65 ppm.

EXAMPLE 26

2,3-Bis(1,1,2,2-Tetrahydroperfluorodecylthio)propan-1-ol (8.13 g; 0.008 mole) and Tonco 70 (a commercial mono-isocyanate containing 70% octadecyl isocyanate and 30% hexadecyl isocyanate) (2.30 g; 0.008 mole) were dissolved in 20 ml urethan grade methyl ethyl ketone in a sealed reaction vessel. As a catalyst, 486 mg of a 1% solution of dibutyltindilurate (8×10$^{-6}$ moles catalyst) in MEK was added and the reactor was heated at 75°, with agitation, for 18 hours. At the end of that period infrared examination showed all —NCO functionality to be absent (no stretching vibration at 2275 cm$^{-1}$) A quantitative yield (10.4 g) urethanes,

and

was obtained as an amber wax by evaportion of the solvent. The product melted at 96° to 104°. The infrared spectrum showed N-H str. at 3335 cm$^{-1}$ and C=O str. at 1694 cm$^{-1}$ Elemental Analysis: Calc'd: C, 38.15; H, 3.85; N, 1.07; F, 49.55: Found: C 38.45; H, 4.07; N, 1.18; F, 49.12.

EXAMPLES 27 to 29

As shown in Table 4 the reaction was extended to include polyfunctional isocyanates and mono and dihydric alcohols.

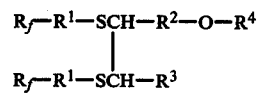

TABLE 4

| Ex.[a] | Wt. (g) | Moles | Iso-cyanate[b] | Wt. (g) | Moles | Catalyst[c] Wt. of 1% solution | Moles | Reac[d] tion time (hrs) | Yield[e] | Elemental analysis Calc'd. | Found | MP °C. |
|---|---|---|---|---|---|---|---|---|---|---|---|---|
| 27 | 8.13 | 0.008 | TMDI | 0.84 | 0.004 | 486 mg. | $8 \times 10^{-6}$ | 36 | 9.3 g. | C 30.52<br>H 2.07<br>N 1.24<br>F 57.59 | 30.47<br>2.27<br>1.22<br>56.89 | 46–53° |
| 28 | 8.13 | 0.008 | HDI | 0.68 | 0.004 | 486 mg. | $8 \times 10^6$ | 36 | 9.1 g. | C 29.47<br>H 1.83<br>N 1.27<br>F 58.69 | 29.91<br>1.82<br>1.39<br>58.17 | softens<br>64–76°<br>melts<br>145° |
| 29 | 8.13 | 0.008 | Desmo-dur RF | 1.11 | 0.027 | 486 mg. | $8 \times 10^6$ | 36 | 7.8 g. | C<br>H<br>N<br>F | | |

[a] = Alcohol used in Examples 27-29
$C_8F_{17}CH_2CH_2SCHCH_2OH$
  |
$C_8F_{17}CH_2CH_2SCH_2$

[b] = TMDI - 1:1 mixture of 2,2,4-trimethyl and 2,4,4-trimethylhexamethylene-1,6-diisocyanate
HDI - hexamethylene-1,6-diisocyanate
Desmodur RF - thiophosphoryl bris(4-phenylisocyanate).
[c] = Reaction temperature in each case is 75°.
[d] = catalyst - dibutyltindilaurate
[e] = Product Structures Ex 27 $C_8F_{17}CH_2CH_2SCHCH_2OCONHCH_2CCH_2CHCH_2CH_2NHCOOCH_2CHSCH_2CH_2C_8F_{17}$
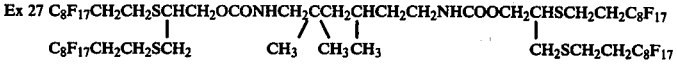

and isomer

Ex 28 $C_8F_{17}CH_2CH_2SCHCH_2OCONH(CH_2)_6NHCOOCH_2CHSCH_2CH_2C_8F_{17}$

Ex 29 $[C_8F_{17}CH_2CH_2SCHCH_2OCONHC_6H_4]_3P=S$

EXAMPLES 30 to 32

The utility of the urethanes of the preceding examples is illustrated in Table 5. The materials were applied to fabrics at a loading of 0.08% and tested for oil and water repellency by the methods already described.

TABLE 6

Evaluation Of Polyurethanes As Oil And Water Repellents Applied At A Level Of 0.08% OWF

| Example | Urethane of Example | Oil Repellency | Water Repellency | Fabric* |
|---|---|---|---|---|
| 30 | 28 | 1 | 0 | Cotton/PE |
| 31 | 29 | 5–6 | 70 | Cotton/PE |
| 32 | 30 | 6 | 70 | Cotton/PE |

*Cotton/PE = 35% cotton, 65% polyester

What is claimed is:

1. A compound of the structure $$R_f-R^1-SCH-R^2-O-R^4$$
$$|$$
$$R_f-R^1-SCH-R^3$$

wherein
$R_f$ is $C_pF_{2p+1}$ or $C_qF_{2q}OC_pF_{2p+1}$, where p is to 12, and q is 2 to 8;
$R^1$ is $C_nH_{2n}$, $C_nH_{2n}SC_nH_{2n}$, $C_nH_{2n}OC_nH_{2n}$ or $C_nH_{2n}NR^5C_nH_{2n}$, where n is 1 to 12 and $R^5$ is H or alkyl with 1 to 6 carbons;
$R^3$ is H or $C_nH_{2n+1}$ where n is 1 to 12;
$R^2$ is $C_mH_{2m}$ or $C_mH_{2m}(OC_kH_{2k})_r$ where m is 0 to 12, k is 2 to 6 and r is 1 to 30; and
$R^4$ is H.

2. A compound of claim 1, wherein
$R^1$ is $-CH_2CH_2-$,
$R_2$ is $-CH_2-$ and
$R^3$ is hydrogen.

3. A compound of claim 1, wherein
$R_f$ is a group of formula $C_pF_{2p+1}$, where p is 6 to 12.

4. A compound of claim 2, wherein $R_f$ is a straight-chain group of formula $C_pF_{2p+1}$, wherein p is 6 to 12.

5. A compound of claim 4, wherein p is 6.

6. A compound of claim 4, wherein p is 8.

7. A compound of claim 4, wherein p is 10.

8. A compound of claim 1, wherein $R^2$ is $C_mH_{2m}(OC_kH_{2k})_r$, where m is 0 to 12, k is 2 to 6 and r is 5 to 30.

9. A compound of claim 3, wherein $R_f$ is a straight chain group.

* * * * *